US00PP27712P3

(12) United States Plant Patent
Ranney

(10) Patent No.: US PP27,712 P3
(45) Date of Patent: Feb. 28, 2017

(54) *CERCIS* TREE NAMED 'NCCC1'

(50) Latin Name: *Cercis canadensis*
Varietal Denomination: NCCC1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 149 days.

(21) Appl. No.: 14/544,063

(22) Filed: Nov. 20, 2014

(65) Prior Publication Data

US 2016/0150703 P1 May 26, 2016

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Keith Robinson
(74) *Attorney, Agent, or Firm* — Myers Bigel, P.A.

(57) ABSTRACT

'NCCC1' is a new cultivar of eastern redbud tree with unique, multi-colored foliage that includes a range and combination of colors including green, white, purple, and pink on emerging and young foliage.

3 Drawing Sheets

Latin name of the genus and species: The Latin name of the novel plant variety disclosed herein is *Cercis canadensis*.

Variety denomination: The inventive variety of the *Cercis canadensis* disclosed herein has been given the varietal denomination 'NCCC1'.

BACKGROUND OF THE INVENTION

The present invention comprises a new and distinct hybrid cultivar of *Cercis canadensis* herein referred to by the cultivar name 'NCCC1'. This new redbud was developed through a breeding program at North Carolina State University, Mills River, N.C. 'NCCC1' was selected from a population of second generation descendants from a hybrid cross between *Cercis canadensis* 'Forest Pansy' (U.S. Plant Pat. No. 2,556) (male parent) and *Cercis canadensis* 'Silver Cloud' (non-patented) (female parent). Plants of the original $F_1$ hybrids between 'Forest Pansy' and 'Silver Cloud' were planted in Mills River, N.C., and isolated from other *Cercis*. Open pollenated seeds were collected from these trees in 2004 and germinated in the spring of 2005. Nineteen seedlings were selected that expressed purple and/or variegated foliage traits and were also planted in Mills River, N.C. 'NCCC1', originally designated as H2005-055-003, was selected primarily for its attractive multi-colored foliage in spring and early summer. The first asexual propagation of 'NCCC1' was carried out in 2009 by budding at a nursery in Belvidere, Tenn. 'NCCC1' has been found to retain its distinctive characteristics, through repeated asexual propagation, over a 9-year period.

SUMMARY OF THE INVENTION

The following are the unique and distinguishing characteristics of this new cultivar when grown under standard horticultural practices at North Carolina State University, Mills River, N.C.: emerging and young leaves express a range and combination of colors including green, white, purple, and pink.

BRIEF DESCRIPTION OF THE DRAWINGS

This new redbud is illustrated by the accompanying photographs which show the plant's foliage and inflorescences. The colors shown are as true as can be reasonably obtained by conventional photographic procedures. Colors in the photographs may differ slightly from the color values cited in the detailed botanical description, which accurately describe the colors of the new redbud.

DETAILED BOTANICAL DESCRIPTION

Figure 1:
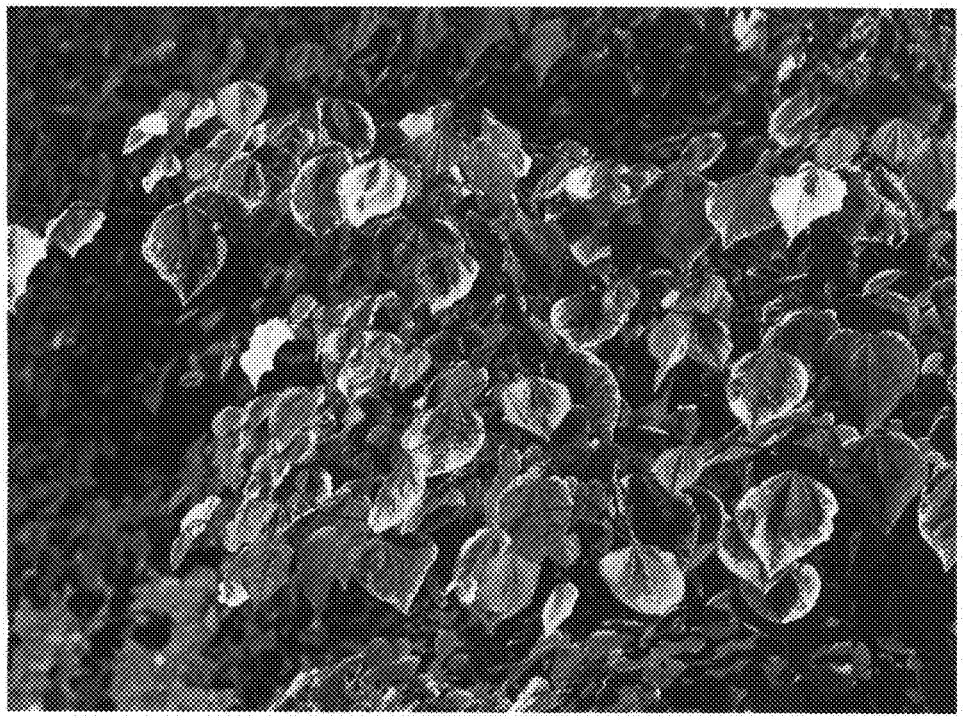
FIG. 1 is a color photograph showing the emerging and young leaves of 'NCCC1' on a 4-year-old tree in Mills River, N.C. on May 28, 2009.
Figure 2:
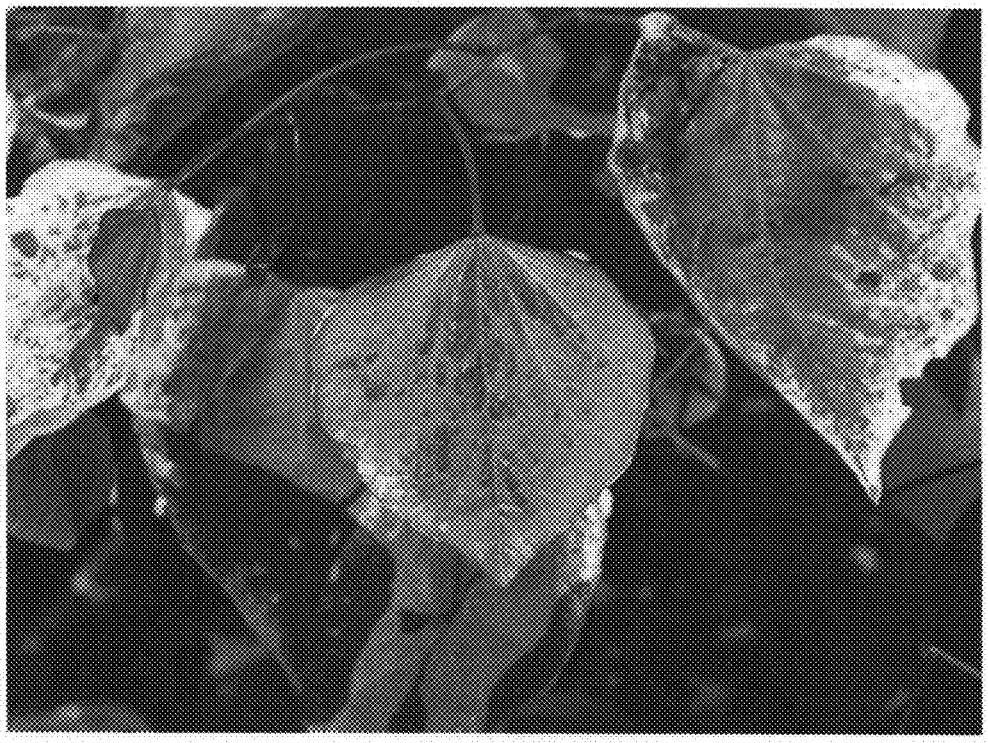
FIG. 2 is a color photograph showing the color of emerging and young leaves of 'NCCC1' on a 4-year-old tree in Mills River, N.C. on May 28, 2009.
Figure 3:
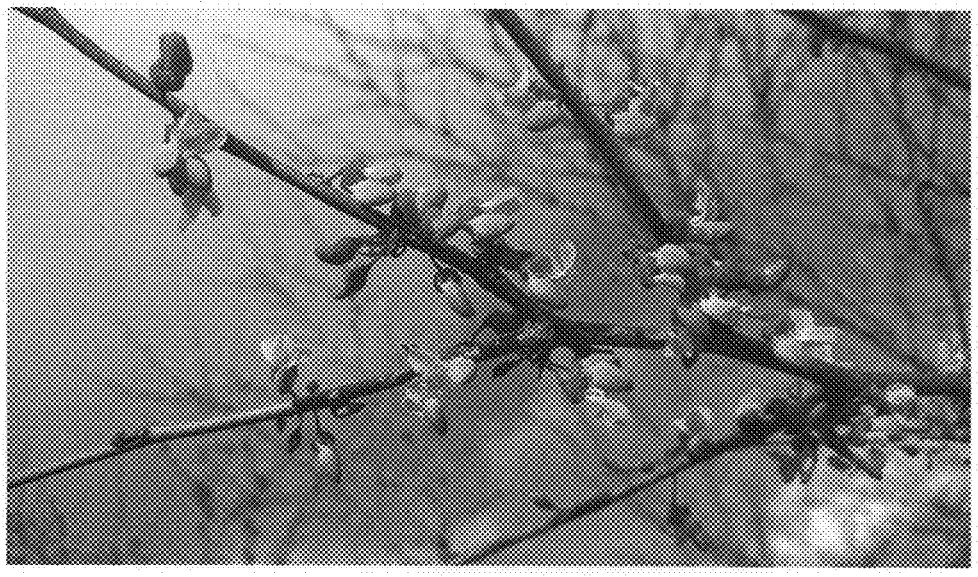
FIG. 3 is a color photograph showing flowers of 'NCCC1' on a 9-year-old tree in Mills River, N.C. on Apr. 15, 2014.

The following is a detailed description of the botanical characteristics of the new and distinct variety of the redbud tree known by the denomination 'NCCC1'. The detailed description was taken on an eight-year-old field-grown tree in Mills River, N.C. in April-October of 2013. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Cercis canadensis* 'NCCC1'.

*Common name.*—Redbud.

Parentage: A second-generation hybrid that resulted from the original cross pollination of *Cercis canadensis* 'Forest Pansy'×*Cercis canadensis* 'Silver Cloud'.

Plant description:

*Plant habit*.—Upright to spreading.
*Height*.—4 meters high after 9 years.
*Spread*.—3 meters wide after 9 years.

Trunk:

*Diameter*.—14 cm. at 30 cm. above the ground.
*Bark surface*.—Rugose.
*Color*.—Brown (N200A) to greyed-green (198).

Stems:

*Color*.—Brown-tan (N200A).
*Length*.—Approximately 44 cm per year of growth.
*Surface*.—Glaucous.
*Lenticels*.—Numerous (1.5 to 2 per $mm^2$), round, greyed-orange (165C).

Foliage:

*Type*.—Deciduous.
*Leaf arrangement*.—Alternate.
*Leaf shape*.—Cordate to reniform.
*Leaf division*.—Simple.
*Leaf base*.—Cordate.
*Leaf apex*.—Cuspidate.
*Leaf venation*.—Reticulate.
*Leaf surface*.—Glaucous (upper and lower).
*Leaf margin*.—Entire.
*Leaf attachment*.—Petiolate.
*Petiole diameter*.—4-8 cm.
*Petiole length*.—2-6 cm.
*Petiole shape*.—Round.
*Petiole color*.—N79A Deep purple.
*Petiole surface*.—Glabrous.
*Stem diameter*.—20 cm in diameter measured 30 cm from the ground on an 11 year old tree.
*Stem internode length*.—About 3 cm.
*Stem aspect*.—About 45 degrees.
*Stem strength*.—Strong.
*Leaf color*.—Emerging (<25% mature size). Upper surface: Purple (N77A) to red-purple (N67B). Lower surface: Red-purple (59A). Intermediate (26 to <75% mature size): Upper surface: Green (139A) speckling or throughout central portion of lamina with red-purple (N67C, 67C and 67D) to white (N155B to N155C) throughout or towards the margin. Lower surface: Purple (N77A to N77C) with some green (139A) speckling or blotches and white (N155B to N155C) typically towards the margins. Mature (76-100% mature size): Upper surface: Green (139A) with some white (N155C) mostly along the margins. Lower surface: Purple (N77A to N77C) to green (139A) with some white (N155C) along the margins. Leaf length: 7 cm to 10 cm (from leaf tip to base of leaf blade). Leaf width: 7 cm to 10 cm (widest portion).

Flowers:

*Flowering season*.—Early to mid-April in Mills River, N.C.
*Inflorescence*.—Papillonaceous flowers arranged in a cluster.
*Number of flowers per cluster*.—2 to 7.
*Arrangement*.—Sessile clusters.
*Location*.—Nodes of previous season growth and along older stems.
*Length of bloom*.—2 to 3 weeks.
*Flower length*.—1 cm.
*Flower width*.—3 cm to 4 cm.
*Flower depth*.—6 mm.
*Pedicel length*.—1-2 cm.
*Pedicel diameter*.—0.5 mm.
*Pedicel shape*.—Round.
*Pedicel color*.—Purple Group (71A).
*Pedicel surface*.—Smooth.
*Pedicel strength*.—Medium.
*Persistence*.—Self-cleaning.
*Flower habit*.—Sparse.
*Fragrance*.—Lacking.

Flower bud:

*Shape*.—Broadly oval.
*Color*.—Purple Group (N77A).
*Surface*.—Smooth.
*Diameter*.—1 mm to 1.5 mm.
*Length*.—4 mm to 5 mm.

Petals:

*Number*.—5, lower 2 fused.
*Color*.—Red-purple (N74B to N66D).
*Petal surface*.—Smooth (both surfaces).
*Petal margin*.—Entire.
*Petal length*.—1 cm.
*Petal width*.—4 cm.
*Petal shape*.—Oblong.
*Apex*.—Rounded.
*Base*.—Cuneate.

Calyx:

*Shape*.—Vase.
*Length*.—4 mm.
*Diameter*.—5 mm.
*Color*.—Purple (71A).
*Surface*.—Smooth.

Sepals:

*Number*.—1 fused.
*Color*.—Red-purple (N66B).
*Surface*.—Smooth.

Reproductive organs:

*Pistil*.—1 cm long, 1-2 mm wide. Color: Red-Purple (59B). Surface: Smooth. Number: 1.
*Stigma*.—Shape: Elliptical. Length: Less than 1 mm. Width: Less than 1 mm. Color: Red-Purple (59B).
*Style*.—Length: Less than 1 mm. Width: Less than 1 mm. Color: Red-purple (60D).

Stamens:

*Number*.—10.
*Length*.—8 mm.
*Width*.—Less than 1 mm.
*Color*.—(Filament) Red-purple (59D).

Anthers:

*Shape*.—Round to oblong.
*Length*.—Less than 1 mm.
*Color*.—Red-purple (59B).

Pollen:

*Color*.—Yellow (9B), abundant.

Ovary: Superior position, elongate shape.

*Length*.—1 cm.
*Width*.—1 cm.
*Color*.—Red-purple (59B).

Fruit:

*Type*.—Legume pod; rarely formed due to low fertility.

Disease and insect resistance: No significant disease or insect pests have been observed.

Cold hardiness: At least USDA zone 6b; not tested in colder zones.

COMPARISON WITH PARENTAL SPECIES

Table 1 shows distinguishing characteristics between 'NCCC1' and its parental taxa.

TABLE 1

Comparison of foliage of 'NCCC1' to original parental cultivars.

| Trait | Taxa | | |
|---|---|---|---|
| | 'Forest Pansy' | 'Silver Cloud' | 'NCCC1' |
| Color of emerging and young | Deep-purple (N77A) to red-purple | White (N155B to N155C) and green (139A) | Emerging with purple (N77A) to red-purple (N67B). Developing more green |

TABLE 1-continued

Comparison of foliage of 'NCCC1' to original parental cultivars.

| Trait | Taxa | | |
|---|---|---|---|
| | 'Forest Pansy' | 'Silver Cloud' | 'NCCC1' |
| foliage (upper surface) | (59A) | in various proportions. | (139A) speckling or throughout central portion of lamina with red-purple (N67C, 67C and 67D) to white (N155B to N155C) throughout or towards the margin of young leaves. |

What is claimed is:

1. A new and distinct hybrid of eastern redbud tree named 'NCCC1', illustrated and described within.

* * * * *